United States Patent
Richardson

(10) Patent No.: US 6,797,291 B2
(45) Date of Patent: Sep. 28, 2004

(54) STABLE HYGROSCOPIC COMPOSITIONS AND METHODS FOR STABILIZING HYGROSCOPIC INGREDIENTS

(75) Inventor: Paul H. Richardson, Vernon, NJ (US)

(73) Assignee: Balchem Corporation, Slate Hill, NY (US)

( * ) Notice: Subject to any disclaimer, the term of this patent is extended or adjusted under 35 U.S.C. 154(b) by 128 days.

(21) Appl. No.: 10/043,085

(22) Filed: Jan. 9, 2002

(65) Prior Publication Data

US 2003/0129295 A1 Jul. 10, 2003

(51) Int. Cl.$^7$ ................................................. A23K 1/18
(52) U.S. Cl. .......................... 426/2; 426/98; 426/307; 426/601; 426/623; 426/807; 424/438
(58) Field of Search ........................ 426/2, 98, 307, 426/601, 807, 623; 424/438

(56) References Cited

U.S. PATENT DOCUMENTS

| | | | |
|---|---|---|---|
| 3,265,629 A | 8/1966 | Jensen | 252/316 |
| 3,619,200 A | 11/1971 | Ferguson et al. | 99/2 |
| 3,655,864 A | 4/1972 | Grass et al. | 424/38 |
| 3,697,640 A | 10/1972 | Grant et al. | 424/35 |
| 3,959,493 A | 5/1976 | Baalsrud et al. | 426/2 |
| 4,181,710 A | 1/1980 | Dannelly et al. | 424/33 |
| 4,196,187 A | 4/1980 | Dannelly et al. | 424/21 |
| 4,216,234 A | 8/1980 | Rawlings et al. | 426/2 |
| 4,533,557 A | 8/1985 | Maruyama et al. | 426/61 |
| 4,713,245 A | 12/1987 | Ando et al. | 424/438 |
| 4,808,412 A | 2/1989 | Smith et al. | 424/442 |
| 4,832,967 A | 5/1989 | Autant et al. | 426/96 |
| 4,837,004 A | 6/1989 | Wu et al. | 424/438 |
| 4,842,863 A | 6/1989 | Nishimura et al. | 424/438 |
| 4,876,097 A | 10/1989 | Autant et al. | 426/74 |
| 4,948,589 A | 8/1990 | Iijima et al. | 424/438 |
| 4,983,403 A | 1/1991 | Ardaillon et al. | 426/2 |
| 5,093,128 A | 3/1992 | Draguesku et al. | 424/438 |
| 5,098,718 A | 3/1992 | Ardaillon et al. | 426/2 |
| 5,186,937 A | 2/1993 | Sparks et al. | 424/438 |
| 5,190,775 A | 3/1993 | Klose | 426/2 |
| 5,206,049 A | * 4/1993 | Fielding et al. | 426/649 |
| 5,227,166 A | 7/1993 | Ueda et al. | 424/438 |
| 5,244,669 A | 9/1993 | Satoh et al. | 424/438 |
| 5,279,832 A | 1/1994 | Greissinger et al. | 424/438 |
| 5,429,832 A | * 7/1995 | Ueda et al. | 426/96 |
| 5,496,571 A | * 3/1996 | Blagdon et al. | 426/2 |
| 5,540,932 A | 7/1996 | Lanter et al. | 424/442 |
| 5,571,527 A | * 11/1996 | Nishimura et al. | 424/438 |
| 5,589,187 A | 12/1996 | Wentworth et al. | 424/439 |
| 5,616,339 A | 4/1997 | Prud'Homme et al. | 424/438 |
| 5,635,198 A | 6/1997 | Nishimura et al. | 424/438 |
| 5,676,966 A | * 10/1997 | Kitamura et al. | 424/438 |
| 5,807,594 A | * 9/1998 | King et al. | 426/2 |
| 5,869,083 A | 2/1999 | Porter | 424/438 |
| 5,928,687 A | 7/1999 | Meade et al. | 426/2 |
| 6,013,286 A | 1/2000 | Klose | 426/2 |
| 6,083,520 A | 7/2000 | Toneby | 424/420 |

* cited by examiner

Primary Examiner—C. Sayala
(74) Attorney, Agent, or Firm—Hoffman & Baron, LLP

(57) ABSTRACT

The present invention provides methods and compositions for providing controlled protection for hygroscopic ingredients that will be exposed to moist or humid environments for significant periods of time by encapsulating the hygroscopic ingredients with a controlled-protection lipid coating. The methods and compositions are particularly useful for stabilizing a hygroscopic bioactive substance, such as choline chloride or lysine hydrochloride, in an animal feed composition and also providing adequate rumen protection in ruminant feeds.

59 Claims, No Drawings

STABLE HYGROSCOPIC COMPOSITIONS AND METHODS FOR STABILIZING HYGROSCOPIC INGREDIENTS

BACKGROUND OF THE INVENTION

This invention relates to methods and compositions for providing hygroscopic substances in a form which is stable in a moist environment. More specifically, the invention is directed to methods and compositions for stabilizing hygroscopic bioactive ingredients, such as choline chloride or lysine hydrochloride, in an animal feed composition and also providing significant rumen protection for the ingredient.

It has been widely established that significant increases in animal feeding efficiencies can be obtained by the use of certain feed additives. This has been particularly true in the feeding of polygastrics where it is now the usual practice to supplement the diet with such materials as vitamins and amino acids. The amino acids represent a particularly useful group of additives since they are the units from which protein molecules are constructed. Although many biologically active materials are employed as feed additives, it is recognized that many of these are inefficiently utilized by ruminants due to degradation thereof in the rumen. Thus, materials such as individual amino acids and certain vitamins are not used routinely in ruminant feeds because of their susceptibility to ruminal degradation.

The rumen, which is essentially a continuous fermenter, supports a variety of micro-organisms under neutral conditions (pH=5-8) which attack and digest much of the feed as part of their normal life cycle. The rumen micro-organisms use the feed to synthesize microbial protein. A stream of ingesta, rich in microbial cells, passes out of the rumen into the omasum. The function of the omasum is to separate liquids and solids. Much of the liquid reenters the rumen while the remainder of the material enters the abomasum or true stomach. Digestion and absorption then proceed in the abomasum in a manner similar to that found in monogastrics. Enzymes secreted into the lumen of the abomasum digest much of the material, including some of that contained in the microbial cells.

The rumen has the great advantage of being able to convert by microbial action many feed components which have no direct nutritive value for the host into products which can be assimilated and utilized by the host. For example, urea may be converted to microbial protein which subsequently may be digested and utilized by the host animal. Cellulose may be converted to a mixture of volatile fatty acids which can serve as a source of energy to the host.

Unfortunately, this microbial action also presents certain disadvantages. For instance, soluble proteins of high nutritive value may be digested and deaminated in the rumen and in part resynthesized into microbial protein of lower nutritive value. Amino acids, the units from which protein molecules are constructed, are also chemically changed by the rumen microorganisms which convert amino acids to carbon dioxide, volatile fatty acids, and ammonia. Ultimately, it is difficult to provide targeted amino acid supplementation to ruminants, as the fed amino acid profile will not match the profile of amino acids presented for digestion and absorption in the small intestine.

It is well recognized in the art that this microbial activity of the rumen limits the productivity of ruminants. Consequently, a great deal of effort has been expended towards providing a bioactive substance in a form which will pass through the rumen essentially unaltered, yet undergo disintegration and absorption in the abomasum.

Numerous patents disclose coating bioactive substances with material which survives the rumen but degrades in the abomasum. For example, Ando U.S. Pat. No. 4,713,245 discloses a rumen-surviving granule comprising a core of bioactive material, a coating substance stable at neutral pH (as found in the rumen) but dissolved or disintegrated at pH=3 (as found in the abomasum), and at least one other coating selected from the group consisting of fatty acids having at least 14 carbon atoms and waxes, animal fat, and vegetable fat having a melting point of 40° C. or higher.

Autant U.S. Pat. No. 4,832,967 discloses a two-layer rumen-surviving coating for water-soluble bioactive substances. The resulting particulate is stable at pH at least as high as 5.5, and releases bioactive substance at pH of 3.5 or less. The coating medium comprises a first coating layer consisting of material sensitive to pH variations and a second coating layer consisting of a hydrophobic composition which must include inorganic filler if the bioactive core has not undergone a surface treatment (application of hydrophobic binder). This hydrophobic outer coating layer is provided with a texture which permits diffusion or penetration of the external liquid medium. The outer coating preferably contains a mixture of hydrophobic substances.

Autant U.S. Pat. No. 4,876,097 discloses a coating composition which is stable at pH less than or equal to about 3.5. The coating comprises a film-forming, water-insoluble binder which contains a substance which controls hydrophilicity, and optionally a substance which is sensitive to pH. Both waxes (hydrophobic) and propylene glycol (water-soluble) are suitable for controlling the hydrophilic/hydrophobic balance. Controlling the hydrophilicity of the particle is said to limit release of the bioactive material in neutral or slightly acidic media, i.e., in the rumen. In very acidic media, i.e., the abomasum, pH-sensitive fillers are activated by the media, which diffuses slowly at a rate established by the hydrophilicity of the coating. The resulting dissolution or swelling of the pH-sensitive filler degrades the coating and releases the bioactive material.

Sibbald U.S. Pat. No. 3,541,204 discloses hydrogenated vegetable and animal fats and waxes such as rice bran wax as coatings which survive the rumen but are disrupted in the intestinal tract.

One well recognized problem with such coatings that can survive the environment of the rumen is that the coated granules tend to float on the contents of the rumen. If the capsules or granules float for a sufficient period, they will be regurgitated. Regurgitation increases the likelihood that the coating will be compromised or destroyed during rumination. Consequently, many of the above described patents provide for adjustment of the density of the capsule or granule by addition of a high density weighting agent, to ensure that the granule sinks. However, as disclosed by Sibbald, the density must not be so great that the capsule will sink to the floor of the rumen and remain there indefinitely. Sibbald discloses an adjusted density of 0.8 to 2.0, preferably about 1.0 to 1.4, g/cc.

Klose U.S. Pat. No. 6,013,286 recognized that merely adjusting the density of the capsule or granule may not be sufficient, since particles coated with hydrophobic material can float on water (and on the rumen), even though the particles have been densified to a specific gravity greater than that of water (or rumen fluid). As a solution to this problem Klose discloses that a surfactant can be applied to the surface of the hydrophobic coating in a quantity sufficient to ensure that the particles do not float on the rumen.

Although the art has achieved useful compositions for providing bioactive substances in a form which will pass through the rumen without significant degradation, e.g., Klose (U.S. Pat. No. 6,013,286), the compositions utilizing hydrophobic coatings do not offer adequate protection from the rumen if first exposed to moist feeds for any significant period of time. This is a particularly significant problem with hygroscopic bioactive substances. Accordingly, the art teaches in such cases that the animal feed should be top dressed with the coated material, i.e., the coated particles should be added to the animal feed just prior to feeding.

Similar problems exist generally with any hygroscopic ingredient that will be exposed to a moist or humid environment for any significant period of time. Namely, that the coated hygroscopic material will be altered or degraded if exposed to such an environment for a sufficient time. Such exposure generally changes the function of the encapsulate. For example, an encapsulated hygroscopic salt loses its taste-masking function after extended exposure in the moist composition.

Thus, there remains a need for methods and compositions for the controlled protection of hygroscopic materials that will be exposed to a moist or humid environment for significant periods of time prior to their intended use. More specifically, there is a need for methods and compositions for providing controlled protection for hygroscopic bioactive substances in moist animal feeds.

SUMMARY OF THE INVENTION

The present invention is directed to methods and compositions for providing controlled protection for hygroscopic ingredients that will be exposed to moist or humid environments for significant periods of time. The methods and compositions are particularly useful for stabilizing a hygroscopic bioactive ingredient, such as choline chloride or lysine hydrochloride, in an animal feed composition and also providing adequate rumen protection in ruminant feeds.

In one aspect, the invention relates to a method for stabilizing a hygroscopic ingredient in a moist composition, which includes: (a) encapsulating the hygroscopic ingredient with a lipid coating in an amount sufficient to retain at least about 60 wt % of the hygroscopic ingredient after the encapsulated ingredient is combined with the moist composition for a time period of at least about 1 day; and (b) combining the encapsulated hygroscopic ingredient with the moist composition.

The hygroscopic ingredient can be choline chloride or lysine hydrochloride.

The moist composition typically has a water activity of at least about 0.1. Preferably, the moist composition has a water activity in the range of about 0.2 to about 0.9 and, more preferably, in the range of about 0.3 to about 0.7.

The moist composition is preferably an animal feed and, more preferably, a ruminant feed.

Preferably, the encapsulated hygroscopic ingredient is in the form of particles having a core, which includes the hygroscopic ingredient, and a lipid coating.

In one embodiment, the lipid coating consists essentially of hydrogenated vegetable oil, hydrogenated corn oil, hydrogenated cottonseed oil, hydrogenated peanut oil, hydrogenated palm kernel oil, hydrogenated sunflower oil and mixtures thereof. The hydrogenated vegetable oil is preferably hydrogenated soybean oil.

In another embodiment, the lipid coating is primarily hydrogenated vegetable oil mixed with lesser amounts of wax selected from the group consisting of beeswax, petroleum wax, rice bran wax, castor wax, microcrystalline wax, and mixtures thereof. Preferably, the hydrogenated vegetable oil is hydrogenated soybean oil and the wax is beeswax.

In one embodiment, the lipid coating also includes one or more discrete additives which impact the release and/or stability and/or density of the encapsulate. Preferably, the discrete additives are selected from the group consisting of dicalcium phosphate, tricalcium phosphate, salts, iron, sodium aluminosilicate, chitosan, and combinations thereof.

In another embodiment, the lipid coating also includes a surfactant.

Preferably, the lipid coating is present in an amount sufficient to retain at least about 80 wt % and most preferably, at least about 90 wt % of the hygroscopic ingredient.

Preferably, the time period is at least about 1 week, more preferably, in the range from about 1 week to about 8 weeks and, most preferably, in the range from about 2 weeks to about 4 weeks.

In another aspect, the invention relates to a method for controlled protection of a hygroscopic bioactive substance contained in a moist feed composition from the rumen portion of the digestive system of a ruminant. The method includes:

(a) encapsulating the hygroscopic bioactive substance with a lipid coating in an amount sufficient to retain at least about 60 wt % of the hygroscopic bioactive substance after the encapsulated substance is combined with the feed for a time period of at least about 1 week and thereafter passes through the rumen portion of the digestive system of a ruminant;

(b) combining the encapsulated substance with the feed composition;

(c) retaining the combination of the encapsulated substance and feed composition for a time period of at least about 1 week; and (d) feeding the combination of the feed composition and encapsulated substance to the ruminant.

Preferably, the lipid coating is present in an amount sufficient to retain at least about 80 wt %, most preferably, at least about 90 wt % of the hygroscopic substance.

Preferably, the time period is in the range from about 1 week to about 8 weeks and, more preferably, in the range from about 2 weeks to about 4 weeks.

The encapsulating step is preferably carried out by applying a continuous lipid coating to the hygroscopic bioactive substance in a one step process.

In another aspect, the invention is directed to a composition containing a stabilized hygroscopic ingredient which includes:

(a) a moist material; and (b) a hygroscopic ingredient stabilized with a controlled-protection lipid coating in an amount sufficient to retain at least about 60 wt % of the hygroscopic ingredient after a time period of at least about 1 day.

The present invention provides methods and compositions useful for protecting hygroscopic ingredients or materials from environmental conditions, e.g., a moist or humid environment, that would otherwise alter the encapsulated hygroscopic material from its intended use. More specifically, the invention provides methods and compositions for stabilizing a hygroscopic ingredient in a moist ruminant feed composition for a designated time period and thereafter protecting the hygroscopic ingredient in the rumen portion of the digestive system of a ruminant.

Additional objects, advantages and novel features of the invention will be set forth in part in the description and examples which follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF INVENTION

The present invention includes methods and compositions for providing controlled protection for hygroscopic ingredients that will be exposed to moist or humid environments for significant periods of time. The methods and compositions are particularly useful for stabilizing a hygroscopic bioactive substance, such as choline chloride or lysine hydrochloride, in an animal feed composition and also providing adequate rumen protection in ruminant feeds.

By the terminology "hygroscopic ingredient" is meant an ingredient which will readily absorb moisture or water from the surrounding environment or will otherwise be altered or degraded from its intended use by the presence of water or moisture in the surrounding environment. "Hygroscopic ingredients" include those materials that gain greater than 2% by weight after exposure to 66% relative humidity, at room temperature for 24 hours.

The present invention is particularly useful for ingredients that gain greater than about 5% by weight, more preferably about 10% by weight and most preferably about 15% by weight, after exposure to 66% relative humidity, at room temperature for 24 hours or ingredients that are highly water soluble, i.e., having a water solubility in excess of about 40 g, more preferable about 50 g and most preferably about 60 g, per 100 grams of water at 25° C.

By the terminology "bioactive substance" is meant any substance or mixture of substances which may have any nutritional or medicinal use. Thus bioactive substances can include nutrients, vitamins, minerals, drugs, enzymes, proteins, carbohydrates, peptides, glycoproteins, probiotics, prebiotics, hormones or diagnostic agents. Examples of amino acids include: methionine, lysine, threonine, leucine, isoleucine, tryptophan, phenylalanine, valine and glycine. Examples of amino acid derivatives include: N-acylamino acids, e.g., N-stearoylmethionine, N-oleoylmethionine, the calcium salt of N-hydroxymethylmethionine, lysine hydrochloride, methionine hydroxy analogues and sodium glutamate. Examples of vitamins include: vitamin A, vitamin A palmitate, vitamin A acetate, beta-carotene, vitamin $D_2$, vitamin $D_3$, vitamin E, menadion sodium bisulfite, the B vitamins, e.g., thiamine, thiamine hydrochloride, riboflavin, nicotinic acid, nicotinic acid amide, calcium pantothenate, choline pantothenate, pyridoxine hydrochloride, choline chloride, cyanocobalamin, biotin, folic acid and p-aminobenzoic acid. Examples of enzymes include: protease preparation, amylase preparation, mixed enzyme preparation and lipase preparation. Examples of carbohydrates include starch, glucose, and sucrose. Examples of drugs for animal use include: antibiotics such as tetracyclines, aminoglycosides, macrolides, polypeptides, polysaccharides and polyethers, vermifuges such as Negphone, and antiparasitics such as piperazine salts. Examples of hormones include: estrous hormones such as estrogen, stilbestrol and hexestrol, and thyroid hormones such as thyroprotein and goitrogen.

Although these substances are generally used alone, they may also be used in combination as a mixture.

In regard to ruminants, "bioactive substance" includes any of the bioactive substances described above which are beneficial to the ruminant upon passing the rumen and reaching the abomasum and/or intestine.

By the terminology "hygroscopic bioactive ingredient (or substance)" is meant any of the bioactive substances described above which will readily absorb moisture or water from the surrounding environment or whose activity or usefulness will be diminished in such an environment.

By the terminology "moist composition," which includes moist materials or feeds, is meant a material having a moisture content that would alter the encapsulate containing the hygroscopic ingredient or substance over time. In other words, the moist composition or feed has a water activity sufficiently high to cause the encapsulate containing the hygroscopic ingredient or substance to absorb water or to be otherwise altered or diminished from performing its intended purpose over a period of time.

The water activity of the moist composition is typically in excess of 0.1. Preferably, the water activity of the composition is in the range of about 0.2 to about 0.9 and, more preferably, about 0.3 to about 0.7. Animal feeds typically have a water content of up to about 15% water and a water activity in the range of about 0.3 to about 0.7.

In accordance with the present invention, particles or granules of the hygroscopic substance are encapsulated in a lipid coating. The lipid coating substantially protects the hygroscopic materials from a moist or humid environment for a designated period of time. In the case of a moist composition containing a hygroscopic ingredient, the coating must substantially protect the ingredient from the moist composition for a designated period of time.

The lipid coating provides the required protection for the hygroscopic substance in the absence of any other required protective coatings, such as, for example, required polymeric materials.

In the same way, particles or granules of the bioactive substances discussed above are encapsulated with a lipid coating.

A requirement for the lipid coating material in a ruminant feed is to substantially prevent release of the bioactive substances into the rumen portion of the digestive system. The coating must be essentially insoluble and impermeable in the rumen and must have a melting point higher than the temperature of the rumen fluid (e.g., about 40° C.).

Another requirement for the lipid coating material in a ruminant feed is to have the ability to withstand feed environment or storage conditions of relatively high humidity and a broad temperature range for a designated period of time without a significant loss of rumen-stability. Typical temperature ranges include −20° C. to 50° C. Thus, the hygroscopic bioactive substance must be essentially protected from the rumen after being stored in the feed material for a designated period of time.

Preferably, the lipid coating will at a minimum have the ability to retain at least about 60 wt % of the hygroscopic ingredients after the encapsulate is placed in water for 5 hours at room temperature. More preferably, the coating will retain at least about 70 wt % and, most preferably, at least about 80 wt %, under such conditions.

Any lipid coating, or mixture thereof, which meets the above described requirements can be used in this invention. Typically, lipids or lipid materials which meet such requirements are materials which are substantially water-insoluble, but soluble in a so-called fat solvent, and which are solid or of wax-like semi-solid consistency at the temperature where protection is desired. The lipid material can include materials which are utilized or not utilized by the animal ingesting it. Examples of such materials include waxes, fatty acids, fatty alcohols, fatty acid esters, sterols, phospholipids and hydrogenated oils.

The wax can be paraffin wax; a petroleum wax; a mineral wax such as ozokerite, ceresin, utah wax or montan wax; a vegetable wax such as, for example, carnuba wax, japan wax, bayberry wax or flax wax; an animal wax such as, for example, spermaceti; or an insect wax such as beeswax, Chinese wax or shellac wax.

Additionally, the wax material can be an ester of a fatty acid having 12 to 31 carbon atoms and a fatty alcohol having 12 to 31 carbon atoms, the ester having from a carbon atom content of from 24 to 62, or a mixture thereof. Examples include myricyl palmitate, cetyl palmitate, myricyl cerotate, cetyl myristate, ceryl palminate, ceryl certate, myricyl melissate, stearyl palmitate, stearyl myristate and lauryl laurate.

The fatty acids can have from 10 to 22 carbon atoms and can be, for example, decenoic, docosanoic, stearic, palmitic, lauric or myristic acid.

The fatty alcohols can have from 14 to 31 carbon atoms and can be, for example, lauryl, cetyl, stearyl, myristyl, myricyl, arachyl, carnubyl or ceryl alcohol.

The fatty acid esters can be mono-, di- or triglyceryl esters formed from fatty acids having from 10 to 22 carbon atoms, such as for example glyceryl distearate, glyceryl tristearate, glyceryl monostearate, glyceryl dipalmitate, glyceryl tripalmitate, glyceryl monopalmitate, glyceryl dilaurate, glyceryl tripalmitate, glyceryl monopalmitate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodecenoate, glyceryl didecenoate or glyceryl tridecenoate.

The sterols can be, for example, cholesterol, stigmasterol or sitosterol.

The phosphatides or phospholipids, can be, for example, lecithin.

Preferred coatings comprise hydrogenated vegetable oils including triglycerides such as hydrogenated cottonseed, corn, peanut, soybean, palm, palm kernel, babassu, sunflower and safflower oils. Preferred hydrogenated vegetable oils include hydrogenated palm oil, cottonseed oil and soybean oil. The most preferred hydrogenated vegetable oil is hydrogenated soybean oil. Other vegetable- and animal-derived fats and waxes also are suitable.

The coating can also include mixtures of different lipids. For example, in addition to the preferred hydrogenated vegetable oils, other ingredients which can be incorporated in the lipid coating include beeswax, petroleum wax, and lower melting hydrogenated vegetable oil blends. Other waxes and oils such as rice bran wax and castor wax also are suitable components in the lipid coating of the present invention.

The method of applying the coating to the granule is not critical, forms no part of the present invention, and may be performed in any manner so long as the coating meets the requirements discussed above. For instance, the granules may be suspended in the liquid coating and the suspension sprayed into a "freezing chamber." Alternatively, the granules may be sprayed with the coatings of the present invention, the granules being suspended by a flow of air (fluidized bed). U.S. Pat. Nos. 4,511,584 at columns 3–5 and 4,511,592 at column 4, the disclosures of which are incorporated herein by reference, teach preferred methods of applying fat coatings to granular particles. U.S. Pat. Nos. 4,537,784 at columns 4–4; 4,497,845 at column 4; U.S. Pat. Nos. 3,819,838; 3,341,446; 3,279,994; 3,159,874; 3,110,626; 3,015,128; 2,799,241; and 2,648,609, which disclosures are all incorporated herein by reference, teach additional methods and apparatus for applying coatings which may be used to produce the coated granules used in the present invention.

In another method, the hygroscopic material to be coated can be placed in a standard tablet coating pan and the lipid material melted and poured into the rotating pan. The pan is heated to a temperature above the melting point of the lipid material in order to facilitate the even distribution of the lipid material over the surface of the material to be coated. After the lipid material is evenly distributed, the pan and its contents are allowed to cool, with continuing rotation and the lipid material solidifies.

Preferably, the lipid coating is applied in a single step process and in the absence of any required solvents.

This invention is particularly useful for delivering the hygroscopic bioactive substances choline chloride or lysine hydrochloride to ruminants; however, the invention is in no way limited to choline chloride or lysine hydrochloride as the bioactive substances.

Other moist compositions include many different food products such as low fat spreads, bakery goods; personal care products such as toothpaste, shampoos, skin creams; household products and drug delivery systems.

The hygroscopic material is typically provided in a granular or particulate form prior to being coated or encapsulated with the lipid material. The granule or particle can be solely the hygroscopic material or, alternatively, the hygroscopic material on a carrier, e.g., a cereal carrier. The encapsulated granules or particles typically have diameters in the range of about 50 microns to about 1000 microns, although other sizes outside this range are included, depending upon the use. The encapsulate typically has a core, which includes the hygroscopic particle or granule, and the lipid coating.

The lipid coating is applied in an amount sufficient to retain at least about 60 wt % of the hygroscopic ingredient after the encapsulated ingredient is combined with the moist composition for a designated time period. Preferably, the coating is in an amount sufficient to retain at least about 80 wt %, more preferably at least about 90 wt % and, most preferably at least about 95 wt % of the hygroscopic ingredient. The designated period is preferably at least about 1 day, more preferably at least about 1 week and, most preferably, at least about 2 weeks or more.

It may also be desirable, depending upon the application, to apply the lipid coating in an amount sufficient to retain only up to a predetermined amount of the hygroscopic ingredient after the encapsulated ingredient is combined with the moist composition for a designated time period. For example, in order to control the release of a bioactive hygroscopic ingredient at a selected portion of an animal's digestive system, it may be desirable to apply a lipid coating that retains a predetermined amount, e.g., 80 wt %, of the ingredient after the encapsulate is combined with a moist animal feed for a designated time period, e.g., 2 weeks.

Thus, in accordance with the present invention, the predetermined amount of the hygroscopic ingredient retained can be an amount in a range, for example, from about 60 up to about 95 wt %, about 70 up to about 90 wt % or about 70 up to about 80 wt %, depending on the application.

With regard to bioactive ingredients in ruminant feeds, it is important for at least a portion of the hygroscopic bioactive ingredient in the ruminant feed to be released in the post-rumen portion of the digestive system of the ruminant. Preferably, substantially all of the bioactive substance which passes through the rumen will be released in the post-rumen portion. Typically, in order to achieve this, the encapsulated bioactive substance will have to be exposed to (or combined with) the moist feed composition for a period of time prior to being ingested by the ruminant. Thus, the lipid coating is generally applied in an amount that would prevent any significant release of the bioactive substance in the rumen or post-rumen portion of the digestive system, if ingested without first exposing the encapsulate to a moist environment. The amount of the lipid coating applied is determined by the storage time of the feed, i.e., the time period that the encapsulate is combined with the moist feed prior to ingestion by the ruminant.

In the case of a hygroscopic bioactive substance contained in a moist ruminant feed, a controlled-protection lipid coating is applied in an amount sufficient to retain at least 60 wt % of the hygroscopic substance after the encapsulated substance is combined with the feed for a designated period of time and thereafter passes through the rumen portion of the digestive system of the ruminant. Again, the lipid coating is preferably present in an amount sufficient to retain at least about 80 wt % and, more preferably, at least about 90 wt % of the hygroscopic ingredient. Preferably, the time period is at least about 1 week, more preferably, in the range from about 1 week to about 8 weeks and, most preferably, in the range from about 2 weeks to about 4 weeks.

In order to achieve the desired results discussed above, the lipid coating is typically applied to the hygroscopic material in the range from about 40 to about 80 percent by weight, preferably about 50 to about 70 percent by weight based on the total weight of the encapsulate, depending upon the particular hygroscopic material. The bioactive substance, and optionally the carrier, is typically in the range from about 20 to 60 percent by weight, preferably about 30 to about 50 percent by weight based on the total weight of the encapsulate.

According to the present invention, the encapsulates can contain additives whose role is to facilitate the implementation of the techniques for preparing these encapsulates or to improve the physicochemical characteristics. It can be advantageous to add emulsifying agents, agents for improving compatibility, agents that impact the release and/or stability, densification additives or wetting agents. If included, these additives generally represent only a few percent by weight of the coating.

Of the possible additives, the lipid coating will most likely include one or more discrete additives which impact the release and/or stability and/or density of the encapsulate. Preferably, the discrete additives are selected from the group consisting of dicalcium phosphate, tricalcium phosphate, salts, iron, sodium aluminosilicate, chitosan, and combinations thereof. These additives are typically added in the range of 1 to 30 percent by weight.

Suitable wetting agents are also typically included in the encapsulate composition in connection with ruminant feeds. Examples of such wetting agents include, polysorbate 60, polysorbate 80, propylene glycol, sodium dioctylsulfosuccinate, and combinations thereof. Other surface active agents, wetting agents, and emulsifiers such as, but not limited to, sodium lauryl sulfate, lactylic esters of fatty acids, polyglycerol esters of fatty acids, triacetin, and lecithin, are also suitable for use in this invention. The wetting agents are typically added in the range of about 0.01 to about 10 percent by weight, preferably in the range of about 0.1 to about 3.0 percent by weight for polysorbate 60, polysorbate 80, and sodium dioctylsulfosuccinate, and preferably about 1 to about 5 percent by weight for propylene glycol.

Skilled practitioners also recognize that flow agents, such as finely-divided silica, can be admixed with the particles of the invention to facilitate handling.

EXAMPLES

The following non-limiting examples have been carried out to illustrate the preferred embodiments of the invention at the present time. The examples include the preparation of encapsulates containing hygroscopic ingredients and evaluating the protection afforded by the encapsulate coating to various environments.

All encapsulates were prepared as described below. The coating components were melted and mixed together. The substrate was coated by spraying the encapsulate thereon. The iron density modifier was added during the coating process and the wetting agent was added at the end of the coating process. After cooling, the encapsulated product was passed through a six mesh screen to break-up agglomerates.

Example 1

| Composition of Encapsulate | Wt. % |
| --- | --- |
| Bioactive Substrate-<br>70 percent Choline Chloride<br>on cereal carrier | 27.5 |
| Lipid Coating | 64.6 |
| Density Modifier<br>Reduced Iron | 7.5 |
| Polysorbate 80 | 0.4 |

Example 2

| Composition of Encapsulate | Wt. % |
| --- | --- |
| Bioactive Substrate-<br>70 percent Choline Chloride<br>on cereal carrier | 35 |
| Lipid Coating | 57.1 |
| Density Modifier<br>Reduced Iron | 7.5 |
| Polysorbate 80 | 0.4 |

Example 3

| Composition of Encapsulate | Wt. % |
| --- | --- |
| Bioactive Substrate-<br>70 percent Choline Chloride<br>on cereal carrier | 42.5 |
| Lipid Coating | 49.6 |
| Density Modifier | 7.5 |

-continued

| Composition of Encapsulate | Wt. % |
|---|---|
| Reduced Iron | |
| Polysorbate 80 | 0.4 |

Example 4

| Composition of Encapsulate | Wt. % |
|---|---|
| Bioactive Substrate- Lysine HCl | 39.0 |
| Lipid Coating | 57.6 |
| Density Modifier | 3.0 |
| Reduced Iron | |
| Polysorbate 80 | 0.4 |

Example 5

| Composition of Encapsulate | Wt. % |
|---|---|
| Bioactive Substrate- Lysine HCl | 42.0 |
| Lipid Coating | 54.6 |
| Density Modifier | 3.0 |
| Reduced Iron | |
| Polysorbate 80 | 0.4 |

Example 6

| Composition of Encapsulate | Wt. % |
|---|---|
| Bioactive Substrate- Lysine HCl | 50 |
| Lipid Coating | 45.6 |
| Density Modifier | 4.0 |
| Reduced Iron | |
| Polysorbate 80 | 0.4 |

The lipid coating was a mixture of approximately 90 wt % hydrogenated soybean oil and approximately 10 wt % beeswax.

An in-vitro rumen bypass test was performed as follows: A sample of 0.3 grams of the encapsulate material in an Ankom 57 polyfiber bag was added to a solution of 400 mls of rumen fluid and 1600 mls of an in-vitro buffer, at 39° C. Three prepared for each sample. The in-vitro buffer contained the following in distilled water: 1.6 g $NH_4HCO_3$, 14 g $NaHCO_3$, 2.28 g $Na_2HPO_4$, 2.48 g $KH_2PO_4$, 0.24 g $MgSO_4.7H_2O$, 0.264 g $CaCl_2.2H_2O$, 0.2 g $MnCl_2.4H_2O$, 0.02 g $CoCl_2.6H_2O$, 0.16 g $FeCl_3.6H_2O$, 0.002 g Resazurin, 0.49 g cysteine HCl, 0.532 g $Na_2S$, 0.16 g NaOH. After 12 hours, the bag and encapsulate were dried at 60° C. The percentage rumen bypass was calculated based upon the amount of hygroscopic bioactive substance remaining in the Ankom 57 polyfiber bag.

The rumen bypass test was repeated with a second sample of the encapsulates, examples 1–3, except the second sample was first placed in a humidity chamber at 66% relative humidity (RH) at room temperature for 4 weeks.

The results of the two tests are listed below in table 1.

For encapsulates 4–6, the rumen bypass test was repeated. With a second sample set of encapsulates, examples 4–6, 20 grams of each encapsulate was placed in a nylon forage bag and immersed in 1000 g of animal feed, in a sealed container, for 3 weeks at room temperature. The animal feed was commercially available corn meal feed (Agway). The animal feed had a 12% water content, 0.64 water activity and its relative humidity at room temperature in the sealed container used to condition the encapsulates was 60%.

The results of the two tests are listed below in table 2.

TABLE 1

Choline chloride encapsulates.

| Encapsulate | Conditions | % Rumen Bypass |
|---|---|---|
| 1 | Not exposed to moist conditions | 99 |
| 2 | Not exposed to moist conditions | 98 |
| 3 | Not exposed to moist conditions | 85 |
| 1 | 4 weeks at 66% RH | 94 |
| 2 | 4 weeks at 66% RH | 68 |
| 3 | 4 weeks at 66% RH | 22 |

TABLE 2

Lysine hydrochloride encapsulates.

| Encapsulate | Conditions | % Rumen Bypass |
|---|---|---|
| 4 | Not exposed to moist conditions | 98 |
| 5 | Not exposed to moist conditions | 97 |
| 6 | Not exposed to moist conditions | 95 |
| 4 | 3 weeks in feed | 86 |
| 5 | 3 weeks in feed | 81 |
| 6 | 3 weeks in feed | 68 |

A review of tables 1 and 2 reveals that exposure to moist conditions reduces the percent rumen bypass for all encapsulates. Although encapsulate 3 has 85% rumen bypass when it has not been exposed to moist conditions, after storage in a high humidity environment, the percent rumen bypass is significantly reduced to 22%. Only those encapsulates that have a higher percent rumen bypass, >94% in these examples, prior to exposure to a moist animal feed or high humidity environment, have a >60% rumen bypass after exposure to a moist animal feed or high humidity environment.

Thus, while there has been disclosed what is presently believed to be preferred embodiments of the invention, those skilled in the art will appreciate that other and further changes and modifications can be made without departing from the scope or spirit of the invention, and it is intended that all such other changes and modifications are included in and are within the scope of the invention as described in the appended claims.

What is claimed is:

1. A method for including a hygroscopic ingredient in a moist composition for a controlled time period, said method comprising:
    (a) encapsulating said hygroscopic ingredient with a lipid coating in an amount sufficient to retain at least about 60 wt % of said hygroscopic ingredient after said encapsulated ingredient is combined with said moist composition for a time period of at least about 1 week; and (b) combining said encapsulated hygroscopic ingredient with said moist composition for a time period of at least about one week.

2. A method according to claim 1, wherein said hygroscopic ingredient is choline chloride or lysine hydrochloride.

3. A method according to claim 1, wherein said moist composition has a water activity of at least about 0.1.

4. A method according to claim 3, wherein said moist composition has a water activity in the range of about 0.2 to about 0.9.

5. A method according to claim 4, wherein said moist composition has a water activity in the range of about 0.3 to about 0.7.

6. A method according to claim 1, wherein said moist composition is an animal feed.

7. A method according to claim 1, wherein said encapsulated hygroscopic ingredient is in the form of particles comprising a core, which comprises said hygroscopic ingredient, and a lipid coating.

8. A method according to claim 1, wherein said lipid coating consists essentially of hydrogenated vegetable oil, hydrogenated corn oil, hydrogenated cottonseed oil, hydrogenated peanut oil, hydrogenated palm kernel oil, hydrogenated sunflower oil and mixtures thereof.

9. A method according to claim 8, wherein said hydrogenated vegetable oil is hydrogenated soybean oil.

10. A method according to claim 1, wherein said lipid coating is primarily hydrogenated vegetable oil mixed with lesser amounts of wax selected from the group consisting of beeswax, petroleum wax, rice bran wax, castor wax, microcrystalline wax, and mixtures thereof.

11. A method according to claim 10, wherein the wax is beeswax.

12. A method according to claim 1, wherein said lipid coating further comprises one or more discrete additives which impact the release and/or stability and/or density of the encapsulate.

13. A method according to claim 12, wherein said discrete additives are selected from the group consisting of dicalcium phosphate, tricalcium phosphate, salts, iron, sodium aluminosilicate, chitosan, and combinations thereof.

14. A method according to claim 1, wherein said lipid coating further comprises a surfactant.

15. A method according to claim 1, wherein said lipid coating is present in an amount sufficient to retain at least about 80 wt % of said hygroscopic ingredient.

16. A method according to claim 15, wherein said lipid coating is present in an amount sufficient to retain at least about 90 wt % of said hygroscopic ingredient.

17. A method according to claim 16, wherein said lipid coating is present in an amount sufficient to retain at least about 95 wt % of said hygroscopic ingredient.

18. A method according to claim 1, wherein said time period is in the range from about 1 week to about 8 weeks.

19. A method according to claim 1, wherein said time period is in the range from about 2 weeks to about 4 weeks.

20. A method for controlled protection of a hygroscopic bioactive substance contained in a moist feed composition from the rumen portion of the digestive system of a ruminant, said method comprising:

(a) encapsulating said hygroscopic bioactive substance with a lipid coating in an amount sufficient to retain at least about 60 wt % of said hygroscopic bioactive substance after said encapsulated substance is combined with said feed for a time period of at least about 1 week and thereafter passes through the rumen portion of the digestive system of a ruminant;

(b) combining said encapsulated substance with said feed composition;

(c) retaining said combination of said encapsulated substance and feed composition for a time period of at least about 1 week; and (d) feeding said combination of said feed composition and encapsulated substance to the ruminant.

21. A method according to claim 20, wherein said environmentally sensitive substance is choline chloride or lysine hydrochloride.

22. A method according to claim 20, wherein said feed composition has a water activity of at least about 0.1.

23. A method according to claim 22, wherein said feed composition has a water activity in the range of about 0.2 to about 0.9.

24. A method according to claim 23, wherein said feed composition has a water activity in the range of about 0.3 to about 0.7.

25. A method according to claim 20, wherein said encapsulated hygroscopic bioactive substance is in the form of particles comprising a core, which comprises said hygroscopic bioactive substance, and a lipid coating.

26. A method according to claim 20, wherein said lipid coating consists essentially of hydrogenated vegetable oil, hydrogenated corn oil, hydrogenated cottonseed oil, hydrogenated peanut oil, hydrogenated palm kernel oil, hydrogenated sunflower oil and mixtures thereof.

27. A method according to claim 26, wherein said hydrogenated vegetable oil is hydrogenated soybean oil.

28. A method according to claim 20, wherein said lipid coating is primarily hydrogenated vegetable oil mixed with lesser amounts of wax selected from the group consisting of beeswax, petroleum wax, rice bran wax, castor wax, microcrystalline wax, and mixtures thereof.

29. A method according to claim 28, wherein said hydrogenated vegetable oil is hydrogenated soybean oil.

30. A method according to claim 28, wherein the wax is beeswax.

31. A method according to claim 20, wherein said lipid coating is present in an amount sufficient to retain at least about 80 wt % of said hygroscopic substance.

32. A method according to claim 31, wherein said lipid coating is present in an amount sufficient to retain at least about 90 wt % of said hygroscopic substance.

33. A method according to claim 20, wherein said time period is in the range from about 1 week to about 8 weeks.

34. A method according to claim 33, wherein said designated time period is in the range from about 2 weeks to about 4 weeks.

35. A method according to claim 20, wherein said encapsulating step is carried out by applying a continuous lipid coating to said bioactive substance in a one step process.

36. A method according to claim 20, wherein said lipid coating further comprises one or more discrete additives which impact the release and/or stability and/or density of the encapsulate.

37. A method according to claim 36, wherein said discrete additives are selected from the group consisting of dicalcium phosphate, tricalcium phosphate, salts, iron, sodium aluminosilicate, chitosan, and combinations thereof.

38. A method according to claim 20, wherein said lipid coating further comprises a surfactant.

39. A composition containing a stabilized hygroscopic ingredient comprising:
(a) a non-water sensitive moist material; and
(b) a hygroscopic ingredient stabilized against exposure to said moist material for a time period of at least about one week, wherein said hygroscopic ingredient is encapsulated with a controlled-protection lipid coating in an amount sufficient to retain at least about 60 wt % of said hygroscopic ingredient after being exposed to said moist material for a time period of at least about 1 week.

40. A composition according to claim 39, wherein said non-water sensitive material has a water activity of at least about 0.1.

41. A composition according to claim 40, wherein said non-water sensitive material has a water activity in the range of about 0.2 to about 0.9.

42. A composition according to claim 41, wherein said non-water sensitive material has a water activity in the range of about 0.3 to about 0.7.

43. A composition according to claim 39, wherein said non-water sensitive material is an animal feed.

44. A composition according to claim 43, wherein said animal feed is ruminant feed and said lipid coating is present in an amount sufficient to retain at least about 60 wt % of said hygroscopic ingredient after the stabilized hygroscopic ingredient is exposed to said ruminant feed for a time period of at least about one week and thereafter passed through the rumen portion of the digestive system of a ruminant following ingestion of said composition by said ruminant.

45. A composition according to claim 44, wherein said hygroscopic ingredient is choline chloride or lysine hydrochloride.

46. A composition according to claim 39, wherein said lipid coating consists essentially of hydrogenated vegetable oil, hydrogenated corn oil, hydrogenated cottonseed oil, hydrogenated peanut oil, hydrogenated palm kernel oil, hydrogenated sunflower oil and mixtures thereof.

47. A composition according to claim 46, wherein said hydrogenated vegetable oil is hydrogenated soybean oil.

48. A composition according to claim 39, wherein said lipid coating is primarily hydrogenated vegetable oil mixed with lesser amounts of wax selected from the group consisting of beeswax, petroleum wax, rice bran wax, castor wax, microcrystalline wax, and mixtures thereof.

49. A composition according to claim 48, wherein said hydrogenated vegetable oil is hydrogenated soybean oil.

50. A composition according to claim 48, wherein the wax is beeswax.

51. A composition according to claim 39, wherein said lipid coating is present in an amount sufficient to retain at least about 80 wt % of said hygroscopic ingredient.

52. A composition according to claim 51, wherein said lipid coating is present in an amount sufficient to retain at least about 90 wt % of said hygroscopic ingredient.

53. A composition according to claim 52, wherein said lipid coating is present in an amount sufficient to retain at least about 95 wt % of said hygroscopic ingredient.

54. A composition according to 39, wherein said time period is in the range from about 1 week to about 8 weeks.

55. A composition according to claim 54, wherein said time period is in the range from about 2 weeks to about 4 weeks.

56. A composition according to claim 39, wherein said lipid coating further comprises one or more discrete additives which impact the release and/or stability and/or density of the encapsulate.

57. A composition according to claim 56, wherein said discrete additives are selected from the group consisting of dicalcium phosphate, tricalcium phosphate, salts, iron, sodium aluminosilicate, chitosan, and combinations thereof.

58. A composition according to claim 39, wherein said lipid coating further comprises a surfactant.

59. A composition according to claim 45, wherein said lipid coating is present in an amount sufficient to retain at least about 80 wt % of said hygroscopic ingredient.

* * * * *

UNITED STATES PATENT AND TRADEMARK OFFICE
CERTIFICATE OF CORRECTION

PATENT NO. : 6,797,291 B2
DATED : September 28, 2004
INVENTOR(S) : Richardson

It is certified that error appears in the above-identified patent and that said Letters Patent is hereby corrected as shown below:

Title page,
Item [74], *Attorney, Agent, or Firm*, now reads "Hoffman" should read -- Hoffmann --;

Column 11,
Line 53, now reads "three prepared" should read -- three bags were prepared --;

Column 16,
Line 22, now reads " a composition according to 39" should read -- a composition according to claim 39 --.

Signed and Sealed this

Twenty-fourth Day of May, 2005

JON W. DUDAS
*Director of the United States Patent and Trademark Office*